United States Patent [19]

Wand et al.

[11] Patent Number: 5,130,048
[45] Date of Patent: Jul. 14, 1992

[54] FERROELECTRIC LIQUID CRYSTAL COMPOSITIONS CONTAINING CHIRAL HALOALKOXY TAILS UNITS

[75] Inventors: Michael Wand; William N. Thurmes; David Walba, all of Boulder, Colo.

[73] Assignee: Displaytech, Inc., Boulder, Colo.

[21] Appl. No.: 556,656

[22] Filed: Jul. 20, 1990

Related U.S. Application Data

[63] Continuation-in-part of Ser. No. 164,233, Mar. 4, 1980, Pat. No. 5,051,506.

[51] Int. Cl.⁵ .................. C09K 19/52; C07D 239/02; C07D 213/28; C07C 69/76
[52] U.S. Cl. .................. 252/299.01; 252/299.61; 252/299.62; 252/299.64; 252/299.65; 252/299.67; 252/299.66; 544/335; 544/298; 546/339; 560/62; 560/108; 560/109; 568/643; 568/645
[58] Field of Search .......... 252/299.01, 299.61, 252/299.62, 299.63, 299.64, 299.65, 299.66, 299.67; 544/298, 335; 546/339; 560/62, 108, 109; 568/643, 645

[56] References Cited

U.S. PATENT DOCUMENTS

| | | | |
|---|---|---|---|
| 4,556,727 | 12/1985 | Walba et al. | 560/73 |
| 4,695,650 | 9/1987 | Walba et al. | 560/109 |
| 4,725,688 | 2/1988 | Taguchi et al. | 544/298 |
| 4,728,458 | 3/1988 | Higuchi et al. | 252/299.65 |
| 4,777,280 | 10/1986 | Eidman et al. | 558/329 |
| 4,795,587 | 1/1989 | Ohno et al. | 252/299.61 |
| 4,798,680 | 1/1989 | Nohira et al. | 252/299.01 |
| 5,051,506 | 9/1991 | Wand et al. | 544/289 |

FOREIGN PATENT DOCUMENTS

| | | |
|---|---|---|
| 0220747 | 5/1987 | European Pat. Off. |
| 0225236 | 2/1988 | European Pat. Off. |
| 0263437 | 4/1988 | European Pat. Off. |
| 0267585 | 5/1988 | European Pat. Off. |
| 0269062 | 6/1988 | European Pat. Off. |
| 0278665 | 8/1988 | European Pat. Off. |
| 62-111939 | 5/1987 | Japan . |
| 62-258361 | 11/1987 | Japan . |
| 63-264573 | 11/1988 | Japan . |
| 8606373 | 11/1986 | PCT Int'l Appl. |
| 8705018 | 8/1987 | PCT Int'l Appl. |
| 8902425 | 3/1989 | PCT Int'l Appl. |

OTHER PUBLICATIONS

Furukawa et al. (1988) Ferroelectrics 85:451-459.
Chemical Abstract No. 109:201686w (p. 795).

Primary Examiner—Robert L. Stoll
Assistant Examiner—Shean C. Wu
Attorney, Agent, or Firm—Greenlee and Winner

[57] ABSTRACT

The subject application discloses a chiral nonracemic composition of the general formula:

$$R_1-Ar-O-CH_2-C^*HX-C^*HY-CH_2-O-R_2$$

wherein $R_1$ is an achiral tail of two to sixteen carbons; Ar is an achiral FLC core of at least two rings; * denotes a chiral carbon; X and Y are halogens; and $R_2$ is one to ten carbon atoms. The $-O-CH_2-C^*HX-C^*HY-CH_2-O-$ segment comprises the chiral proximal segment of the chiral tail; the proximal segment is selected from the enantiomers 2R,3R-dihalo and 2S,3S-dihalo. $R_2$ is the distal segment of the chiral tail.

11 Claims, No Drawings

FERROELECTRIC LIQUID CRYSTAL COMPOSITIONS CONTAINING CHIRAL HALOALKOXY TAILS UNITS

This invention was made with partial support of the United States Government under National Science Foundation Grant no. ISI8722712. The United States Government has certain rights in this invention.

Relatedness of the Application

This application is a continuation-in-part of U.S. Ser. No.164,233, filed Mar.4, 1988, now U.S. Pat. No. 5,051,506 which is incorporated herein in its entirety by reference.

FIELD OF THE INVENTION

The present invention relates to ferroelectric liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. Since the coupling to an applied electric field by this mechanism is rather weak, the resultant electro-optical response time may be too slow for many potential applications.

Liquid crystal displays have a number of unique characteristics, including low voltage and low power of operation, which makes them perhaps the most promising of the non-emissive electro-optical display candidates available with today's technology. However, slow response and insufficient nonlinearity can impose limitations for many potential applications. The requirement for speed may become especially important in proportion to the number of elements which have to be addressed in a device. This may result in increasingly impractical production costs for the potential use of such devices in flat-panel displays for use in video terminals, oscilloscopes, radar and television screens.

It has been shown by N. A. Clark and S. T. Lagerwall in Appl. Phys. Lett. 36:899 (1980) and in U.S. Pat. No. 4,367,924 that electro-optic effects with sub-microsecond switching speeds are achievable using the technology of ferroelectric liquid crystals (FLCs). Some display structures prepared using FLC materials, in addition to the high speed (about 1,000 times faster than currently used twisted nematic devices) reported by these investigators, also exhibit bistable, threshold sensitive switching, making them potential candidates for light modulation devices including matrix addressed light valves containing a large number of elements for passive displays of graphic and pictorial information, as well as for optical processing applications. A recent review of the applications of FLC devices is given by Lagerwall, S.T. and Clarke, N.A. (1989) Ferroelectrics 94:3–62.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwall, appropriate application of an external electric field results in alignment of the molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density (P), and directly proportional to orientational viscosity. Fast switching speeds are then associated with FLC phases which possess high polarization density and low orientational viscosity.

A basic requirement for application of ferroelectric liquid crystals in such devices is the availability of chemically stable liquid crystal compounds or mixtures which exhibit ferroelectric phases (chiral smectic C) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing smectic C* phases with useful temperature ranges can also be obtained by admixture of chiral, nonracemic compounds, designated ferroelectric liquid crystal dopants into liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture. The components of FLC mixtures can also be adjusted to vary phase transition temperatures or to introduce desired LC phases.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., supra) which contains a 2-methylbutyl chiral tail. Pure DOBAMBC exhibits a smectic C* phase with a ferroelectric polarization of $-3$ nC/cm$^2$.

There are a number of reports of compounds containing phenylbenzoate, diphenyl, phenylpyrimidine and related cores coupled with chiral tail units which possess monotropic smectic C* phases displaying fast switching speeds at room temperature, or which can be employed as FLC dopants to induce high polarization and fast switching speeds when combined in mixtures with FLC host materials.

The following are exemplary reports of such FLC compounds:

Walba et al., U.S. Pat. No. 4,556,727 reports phenylbenzoates having non-racemic 2-alkoxy-1-propoxy tails.

Eidman and Walba, U.S. Pat. No. 4,777,280 report chiral 1-cyanoalkoxy phenylbenzoates. Walba and Razavi, U.S. Pat. No. 4,695,650 report chirally asymmetric reverse ester phenylbenzoates having chiral 1-haloalkyl tail units.

Ohno et al. (1989) U.S. Pat. No. 4,795,587 refers to liquid crystal compounds exhibiting smectic C phases which contain a phenylpyridine core having the formula:

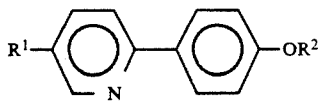

where $R^1$ is an alkyl group having seven to twelve carbon atoms and $R^2$ is an alkyl group having five to twelve carbon atoms.

Japanese patent documents JP 63264573 and JP 62258361 refer to optically active 6-substd.-pyridine-3-carboxylic acid esters useful as ferroelectric smectic liquid crystals. Optically active 6-substituted-pyridine-3-carboxylic acid esters obtained from reaction of dodecyloxybenzoic acid, thionyl chloride and 6-hydroxynicotinic acid (S)-2-methylbutyl ester are specifically referred to. Japanese patent document JP 62175465 refers to ester compounds contained in liquid crystal compositions exhibiting nematic phases. 2-(trans-4-ethyl-cyclohexyl)-5-nicotinic acid-3-fluoro-4-cyanophenyl ester is referred to specifically.

Walba et al. (1986) J. Amer. Chem. Soc. 108:7424–7425 and Walba and Vohra, U.S. Pat. No. 4,648,073 and U.S. Pat. No. 4,705,874 disclose ferroelectric (chiral) smectic liquid crystal compounds having an achiral core and chiral tail units derived from (2,3)-alkyloxiranemethanols which possess a high ferroelectric polarization density. The ferroelectric liquid crystal materials reported have the following general formulas:

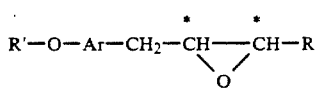

where R is an alkyl of one to seven carbon atoms and R' is an alkyl of five to twelve carbon atoms and Ar is phenylbenzoate or biphenyl.

Hemmerling et al. (1988) European Patent Application, Pub. No. 263437 refers to chiral aryl-2,3-epoxyalkylethers FLC compounds having phenylpyrimidine or phenylpyridazine cores of the formula:

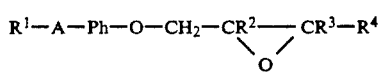

where A is a diazine-2,5,-diyl or diazine-3,6-diyl, $R^1$ is a straight chain or branched alkyl group having 1–12 carbon atoms wherein one or two non-neighboring $CH_2$ groups is replaced with an O or S atom, $R^{2-4}$ are, independent of one another, H, a straight chain alkyl group having 1–12 carbon atoms or a branched alkyl group having 3–10 carbon atoms wherein $R^1$, $R^2$ and $R^3$ are not all H. Compounds in which $R^2$ and $R^3$ are both H having extrapolated polarization densities ($P_{ext}$) in the range from 30–70 nC/cm$_2$ are reported.

Walba and Razavi, U.S. patent application Ser. No. 099,074, now allowed, discloses chirally asymmetric phenyl and biphenylbenzoates having chiral 2,3-epoxy alkyl or 1-halo-2,3-epoxy alkyl tails which are useful as components of FLC materials. The compounds disclosed have the formula:

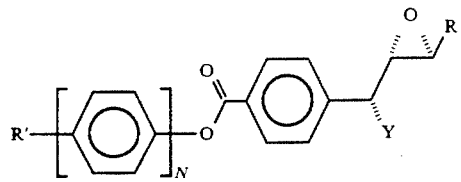

where R' is an alkyl or alkoxyl group having three to fifteen carbon atoms, R is an alkyl group having three to fifteen carbon atoms, n=1 or 2, and Y is a halogen or hydrogen. It is also disclosed, therein, that 1-haloepoxides of formula A can impart higher polarization densities and higher switching speeds in FLC mixtures than their diastereomers of formula B. It is suggested that the difference in properties of A and B is due to the relative alignment of the epoxide and halogen bond dipoles in the isomer.

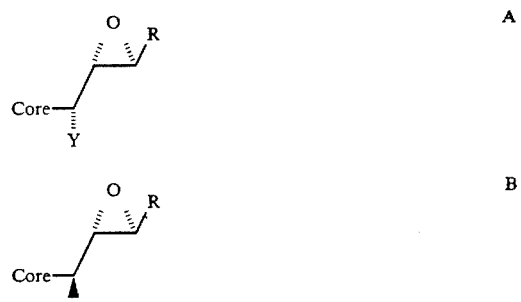

Furukawa, K. et al. (1988) Ferroelectrics 85:451–459 refers to chiral smectic C compounds having an ester group in the core and an optically active tail group, either alkoxy or alkoxy carbonyl, with an electronegative substituent, either a halogen or cyano group, ortho to the chiral tail, for example:

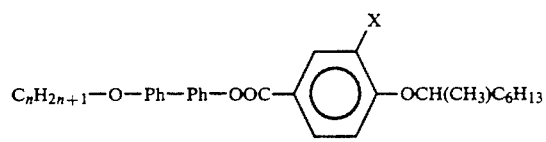

where X=H, Halogen or CN.

Wand et al., U.S. Ser. No. 360,397 discloses methyl epoxides having the formula

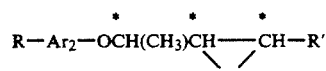

where $Ar_2$ is a phenylbenzoate, biphenyl phenylpyrimidine or phenyl pyridine, R is an alkyl or alkoxy group, and R' is an alkyl group containing 3 to 12 carbon atoms.

While a number of useful ferroelectric liquid crystal materials (both pure compounds and mixtures) have been reported, there is a growing need for FLC materials with varying properties of temperature range, tilt angle and switching speed for use in varied applications. Further, there is a need for FLC dopants with varying mixing properties (which are dependent, at least in part, on chemical composition) for use in the preparation of FLC mixtures. FLC dopants which impart high polarization density to, and retain low viscosity in, such mixtures are of particular interest.

SUMMARY OF THE INVENTION

The present invention provides a class of chirally asymmetric molecules which are useful as components of ferroelectric liquid crystal materials. These compounds can impart the properties of high ferroelectric polarization density and fast electro-optical switching speeds on low polarization materials when mixed with such materials to form ferroelectric liquid crystal compositions. Alternatively, certain of the compounds of the present invention in pure form can also possess stable smectic C* phases having high polarization density.

The composition of the subject invention comprises a chiral nonracemic composition of the general formula:

$$R_1-Ar-O-CH_2-C^*HX-C^*HY-CH_2-O-R_2$$

wherein:

$R_1$ is an achiral tail of two to sixteen carbons; Ar is an achiral FLC core of at least two rings; * denotes a chiral carbon; X and Y are halogens; and $R_2$ is one to ten carbon atoms. The $-O-CH_2-C^*HX-C^*HY-CH_2-O-$ segment comprises the chiral proximal segment of the chiral tail; the proximal segment is selected from the enantiomers 2R,3R-dihalo and 2S,3S-dihalo. $R_2$ is the distal segment of the chiral tail.

The compositions comprising 2R,3R-dihalo and 2S,3S-dihalo proximal segment enantiomers are represented by the following general formulas where $Q=R_2$:

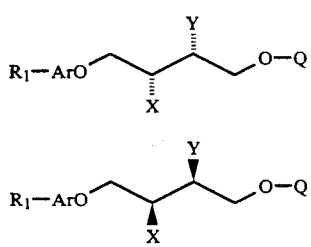

The compositions of the subject invention can be derived from $R_1-Ar-O-CH_2-C^*HX-C^*HY-CH_2-OH$ intermediates, i.e., compounds of formulas IXa and IXb where Q=H. In the final ferroelectric compositions of the subject invention, $Q=R_2$.

X and Y can be the same or different halides. For example, the chiral proximal segment, $-O-CH_2-C^*HX-C^*HY-CH_2-O-$, can be the following regioisomers and their enantiomers:

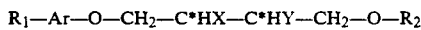

| 2R-fluoro-3R-chloro | 2S-fluoro-3S-chloro |
| 2R-chloro-3R-fluoro | 2S-chloro-3S-fluoro |

2R-fluoro-3R-chloro and 2R-chloro-3R-fluoro are regioisomers; their respective enantiomers, 2S-fluoro-3S-chloro and 2S-chloro-3S-fluoro are also regioisomers.

The achiral cores are rigid, linear moieties. Preferred cores are those that are chemically stable and which do not impart high orientational viscosity in the liquid crystal phase. In the present invention, cores containing at least two aromatic rings are preferred such as those cores based on phenylbenzoates, phenylpyridines, phenylpyrimidines, biphenyls, triphenyls, biphenyl pyridines, biphenylpyrimidines and biphenylbenzoates wherein achiral and chiral tails are located on non-central or outside aromatic rings and are para with respect to the bond of their aromatic ring to the adjacent ring or to the bond of their ring to carbon or oxygen atoms bridging to the adjacent ring. Examples of some of the ferroelectric (FLC) cores useful in the subject invention are illustrated in Table 1. In Table 1, $R_1$ indicates the achiral tail and R* indicates the chiral tail, including the proximal and distal ($R_2$) segments.

As used herein "phenylbenzoate" includes forward and reverse phenylbenzoates:

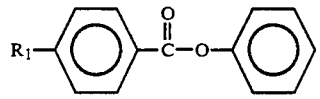

and

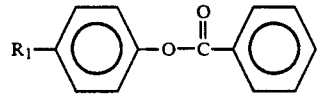

"Phenylpyrimidine" means 2',4-substituted and 5',4-substituted phenylpyrimidines. Additionally, "phenylpyridine" means 2',4-substituted, 3',4-substituted and 5',4-substituted phenylpyridines.

The achiral tail, $R_1$, can be an alkyl, alkenyl or alkoxy group. $R_1$ can contain two to sixteen carbon atoms; it preferably contains five to sixteen carbons; and it most preferably contains eight carbons. $R_1$ can be straight chain or branched. Branching can broaden the smectic C* phase; this effect is enhanced when branching is more distant from the core. It has also been observed that if branching occurs at carbons 2-8 (relative to the

TABLE 1

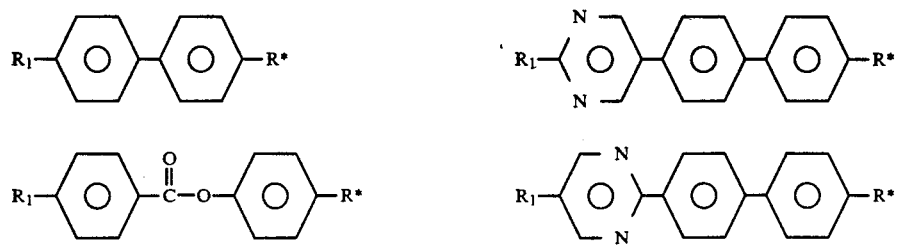

TABLE 1-continued

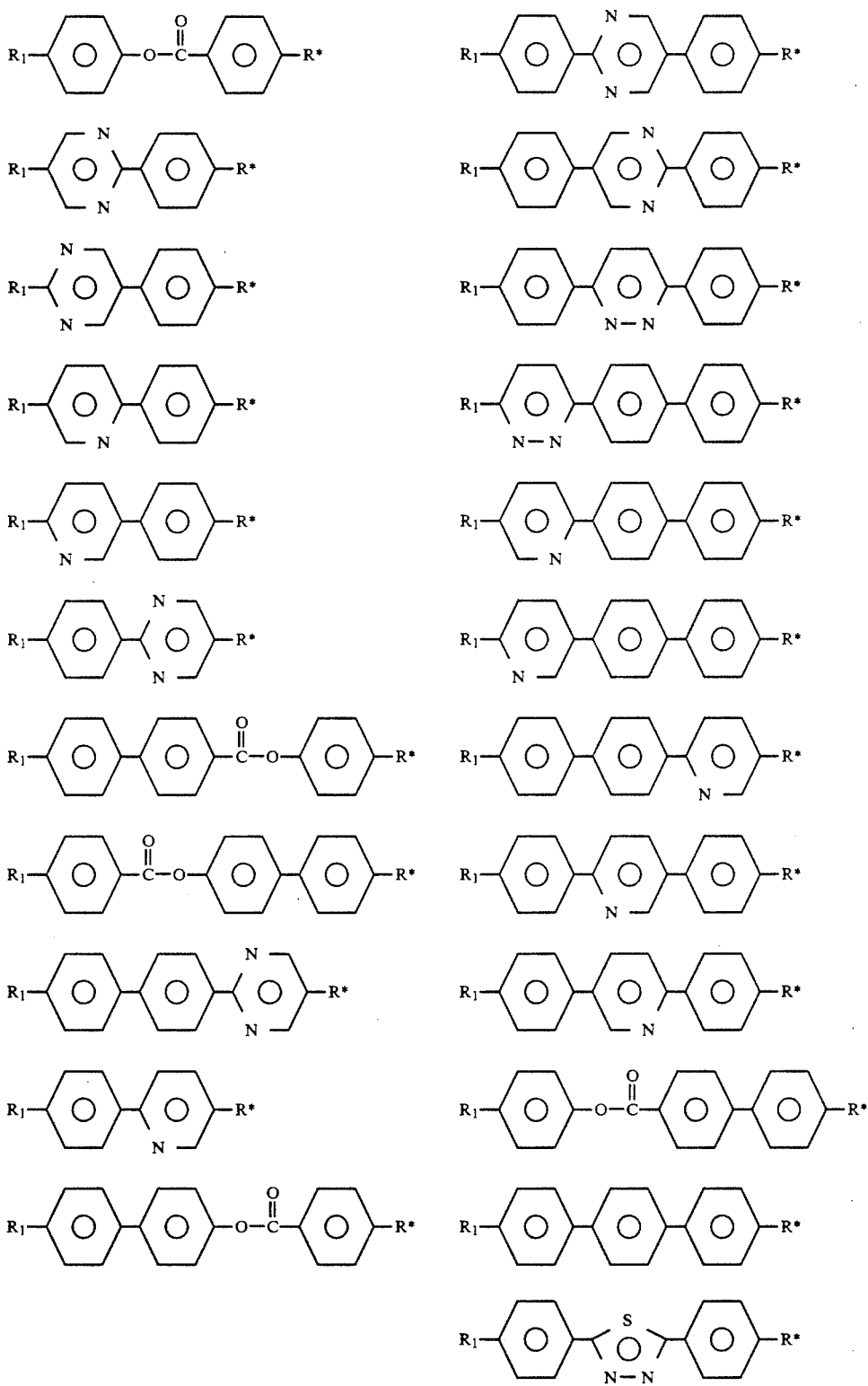

core), polarization density of the FLC molecule is generally not affected.

As described in PCT/EP88/00724 (WO 02425, p.13), oxygen or sulfur atoms can replace non-adjacent CH2 groups in the achiral tail to produce, for example, alkoxy or thiaalkyl tails. It has been observed that such substitutions do not significantly impair the polarization density; such substitutions can impart a broader smectic C* phase of the compound itself or in an FLC mixture containing the compound.

When $R_1$ is an alkenyl, the double bonds can be located at any position in $R_1$'s chain, including the omega position. Positioning of a double bond in the omega position creates a precurser to an FLC polymer. For example, an FLC compound of the subject invention containing an omega-alkenyl achiral tail can be reacted with polysiloxane to form a polymeric FLC.

When $R_1$ is an alkenyl, the double bonds can be cis or trans. However, trans bonds are preferred because cis is likely to result in reduced solubility of the dopant FLC in the host material. Additionally, cis bonds can narrow the smectic C* range.

The halides of the chiral proximal segment are preferably fluorine and chlorine. It has been observed that enantiomers, such as FLC compositions comprising the 2R,3R-difluoro and 2S,3S-difluoro proximal chiral tail segments, function equivalently in FLC host materials except that the sign of their polarization densities is reversed. As will be understood by those in the art, the sign of the polarization of an FLC dopant should be the same as that of the host material in order to achieve high polarization mixtures. It is a feature of this invention that either the IXa (where $Q=R_2$) or the IXb (where $Q=R_2$) enantiomers can be prepared. This allows choice of the appropriate enantiomers for use with a particular host material.

The distal segment ($R_2$) of the chiral tail of the composition of the subject invention can be aldehydes, alkyls, alkyl acyls, alkenyls, alkenyl acyls, alkyl or alkenyl halides and alkyl or alkenyl epoxides. $R_2$ can contain one to ten carbon atoms; as the size of the distal segment increases, it can increase the viscosity of the FLC compound For this reason, it is preferred that $R_2$ contain one to four carbons.

$R_2$ can be straight chain or branched. Branching can broaden the smectic C* phase; generally, this effect is enhanced when branching is more distant from the core.

When $R_2$ is an alkenyl, the double bonds can be cis or trans. However, trans bonds are preferred because cis bonds are likely to result in reduced solubility of the dopant FLC in the host material. Additionally, cis bonds are likely to narrow the smectic C* range.

$R_2$ can contain chiral carbons. Chirality in the distal segment, like that in the proximal segment, contributes to polarization density of the FLC molecule. The distal segment chirality can enhance or reduce the polarization density of the FLC molecule imparted by the proximal segment. The closer the chiral groups in the distal segment to the proximal segment, the greater the impact of the $R_2$ chirality on the dipole created by the proximal segment. Whether a particular chiral $R_2$ enhances or decreases polarization density can be determined by routine testing by known methods of FLC compounds containing the chiral $R_2$ at issue. Syntheses methods of chiral $R_2$ FLC compounds of the subject invention are described hereinbelow and/or are known to those of skill in the art. Methods for measuring polarization density are also described hereinbelow.

Specifically, $R_2$ groups can fall within four subdivisions. The first subdivision is:

$R_2 = CHO$

Compounds having $R_2$ of the first subdivision are synthesized by derivitization method A described hereinbelow. This first subdivision includes compound X of Table 2, i.e., 2-[4'-(2R,3R-difluoro-4-formyl)butyloxy]-phenyl-5-$R_1$-pyrimidine, and its enantiomer.

The second subdivision of distal segments is:

$R_2$ = alkyl or alkenyl acyls.

Compounds having $R_2$ of the second subdivision are synthesized by derivitization method B described hereinbelow. This second subdivision includes, among others, the compounds XI-XVI of Table 2 and their enantiomers. When $R_2$=ethyl acyl, the chiral tail is (2,3-difluoro-4-ethanoate)butyloxy, as exemplified by compounds XI and XII. When $R_2$=propyl acyl, the chiral tail is (2,3-difluoro-4-propanoate)butyloxy, as exemplified by compound XIII. When $R_2$=butyl acyl, the chiral tail is (2,3-difluoro-4-butanoate)butyloxy, as exemplified by compound XIV. When $R_2$=pentyl acyl, the chiral tail is (2,3-difluoro-4-pentanoate)butyloxy, as exemplified by compound XV. When $R_2$=4-pentenyl acyl, the chiral tail is (2,3-difluoro-4-pentenoate)-butyloxy, as exemplified by compound XVI.

The third subdivision of distal segments is:

$R_2$=alkyl, alkenyl and their epoxides.

Compounds having an $R_2$ of the third subdivision are synthesized by derivitization method C described hereinbelow. The third subdivision includes, among others, the compounds XVII-XXI and XXIII of Table 2. When $R_2$=methyl, the chiral tail is (2,3-difluoro-4-methoxy)butyloxy, as exemplified by compound XVII. When $R_2$=butyl, the chiral tail is (2,3-difluoro-4-butyloxy)butyloxy, as exemplified by compound XVIII. When $R_2$=4-pentene, the chiral tail is [2,3-difluoro-4-(4-pentenyloxy)]butyloxy, as exemplified by compound XIX. When $R_2$=1-methylheptyl, the chiral tail is [2,3-difluoro-4-(1-methylheptyloxy)]butyloxy, as exemplified by compound XX. When $R_2$=2R,3R-epoxyhexyl, the chiral tail is [2,3-difluoro-4-(2R,3R-epoxyhexyloxy)]butyoxy, as exemplified by compound XXI. When $R_2$ =2S,3S-epoxyhexyl, the chiral tail is [2,3-difluoro-4-(2S,3S-epoxyhexyloxy)]butyloxy, as exemplified by compound XXIII.

The fourth subdivision is:

$R_2$ = alkyl or alkenyl halides.

Compounds having an $R_2$ of the fourth subdivision are synthesized by derivitization method D described hereinbelow. The fourth subdivision includes, among others, the compounds XXII and XXIV of Table 2. When $R_2$=2R,3R-difluorohexyl, the chiral tail is [2,3-difluoro-4-(2R,3R-difluorohexyloxy)]butyloxy, as exemplified by compound XXII. When $R_2$=2S,3S-difluorohexyl, the chiral tail is [2,3-difluoro-4-(2S,3S-difluorohexyloxy)]butyloxy, as exemplified by compound XXIV.

It is preferred that halides of the distal segment be limited to two. The preferred halides are chlorine and fluorine.

DETAILED DESCRIPTION OF THE INVENTION

The ferroelectric liquid crystal compounds having proximal segments of formulas IXa and IXb (where $Q=R_2$) are prepared from chiral L-diethyl tartrate (Ia) and D-diethyl tartrate (Ib), respectively. Reaction Scheme I illustrates the synthesis of the IXa (Q=H) intermediate from Ia; however, substitution of Ib for Ia produces intermediate compounds of formula IXb (Q=H). The synthesis of compounds IXa or IXb (Q=H) proceed through the formation of a chiral 2,3-isopropylidenethreitol, which is then coupled to a desired 4-substituted core unit ($R_1$—Ar); the resulting compound's ring is opened and treated with halogenating agents to yield the chiral dioxy-2,3-dihalo proximal segment, as exemplified in Scheme I.

As discussed hereinabove, FLC compositions having proximal segments of formulas IXa and IXb (Q=$R_2$) represent a pair of enantiomers. The ferroelectric compounds/dopants comprising these proximal segments function equivalently in FLC materials, except that the sign of P will be reversed. The availability of the different ferroelectric compounds/dopants comprising either the IXa or IXb (Q=$R_2$) proximal segments allows the selection of the appropriate enantiomer for use with a particular host material.

The synthesis method of Scheme I and its analogs are described in detail in the Examples Specifically, the synthesis 2-{[4'-(2R,3R-difluoro-4-hydroxybutyl)oxy]}phenyl-5-hexylpyrimidine (IXa, where $R_1$=hexyl, Q=H, Ar=5,4'-substituted phenylpyrimidine, and X The synthesis of IXa and IXb (Q=H) where X and Y are different halides can also be accomplished by known methods from readily available starting materials. Such regioisomers of IXa and IXb (Q=H) and their enantiomers include:

| 2R-fluoro-3R-chloro | 2S-fluoro-3S-chloro |
|---|---|
| 2R-chloro-3R-fluoro | 2S-chloro-3S-fluoro |

The synthesis of the final ferroelectric compounds, i.e., IXa or IXb (Q=$R_2$), of the present invention from compounds IXa and IXb (where Q=H) can be accomplished by known means as, for example, described herein in the Examples. The Examples describe four derivatization methods designated "A," "B," "C," and "D" in Table 2.

Derivitization method A involves the transesterification of IXa or IXb (Q=H) with methyl formate to form the chiral formyls of the general formula:

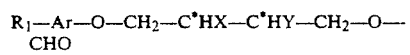

Scheme I

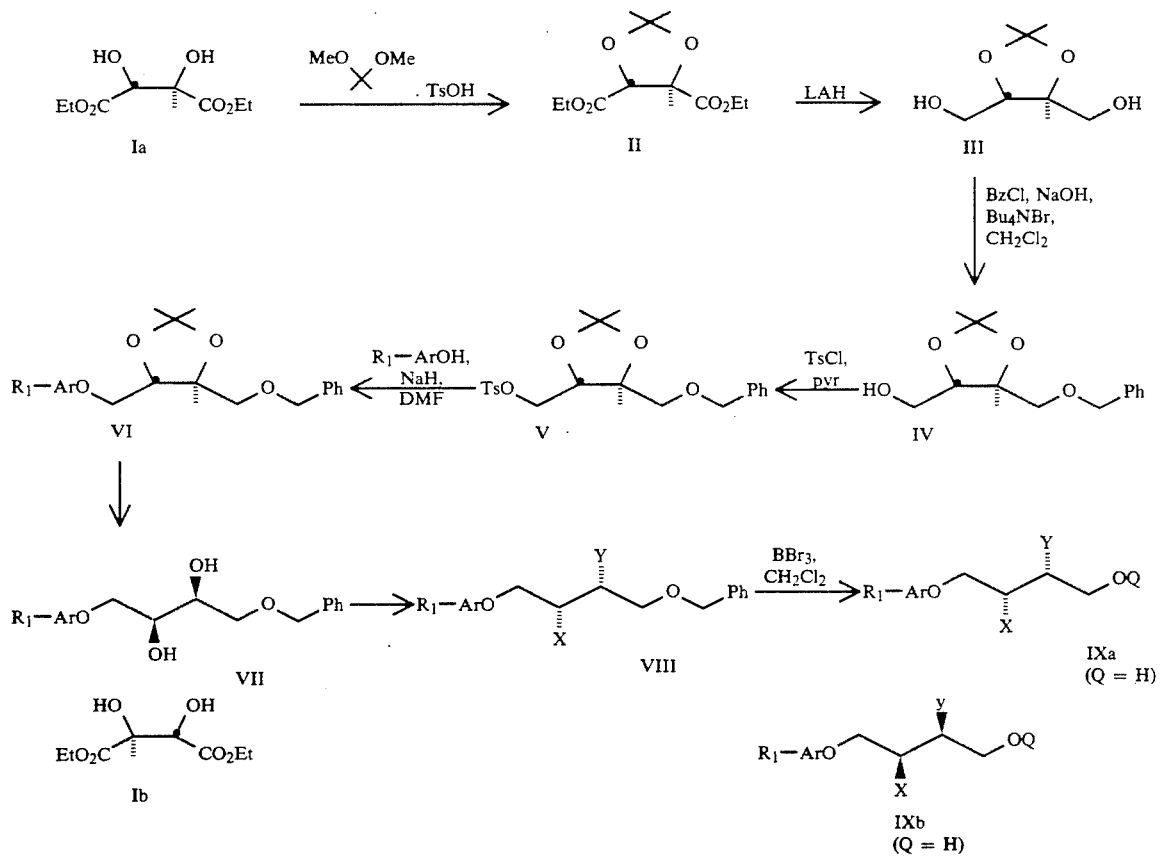

and Y=F) and 2-(4'-[(2S,3S-difluoro-4-hydroxy)-butyloxy])phenyl-5-alkylpyrimidine (IXb, where $R_1$=hexyl, Q=H, Ar=5,4'-substituted phenylpyrimidine, and X and Y=F) are described.

The substituted phenols, $R_1$—ArOH, used in the synthesis of compounds of formula VI of Scheme I, are either commercially available or are produced by known methods from readily available starting materials.

Compound X of Table 2, 4'-[(2R,3R-difluoro-4-formyl)butyloxy]phenyl-5-hexylpyrimidine, exemplifies a compound of A's formula Its synthesis is described in the Examples.

Derivitization method B involves the reaction of compounds of formula IXa or IXb (Q=H) with carboxylic anhydrides, alkanoyl chlorides, or alkenoyl chlorides, to form the esters of the general formula:

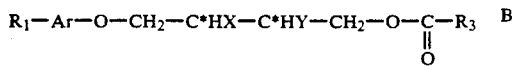

$$R_1-Ar-O-CH_2-C^*HX-C^*HY-CH_2-O-\underset{\underset{O}{\|}}{C}-R_3 \quad B$$

where $R_3$=alkyl or alkenyl.

Some of the compounds produced by derivitization method B include compounds XI-XVI of Table 2. Complete descriptions of synthesis of each compound are provided in the Examples.

Derivitization method C involves the reaction of compounds of formula IXa or IXb (Q=H) with alkyl or alkenyl iodides or alkyl or alkenyl epoxy tosylates to produce the compounds of the general formula:

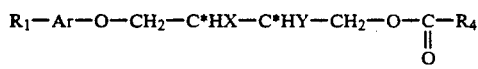

$$R_1-Ar-O-CH_2-C^*HX-C^*HY-CH_2-O-\underset{\underset{O}{\|}}{C}-R_4$$

where $R_4$=alkyl, alkenyl or their epoxies.

Some of the compounds produced by derivitization method C include compounds XVII-XXI and XXIII of Table 2. Complete descriptions of synthesis of each compound are provided in the Examples.

Derivitization method D involves opening the epoxide ring of compounds analogous to XXI or XXIII and treating the resulting intermediate with halogenating agents. The epoxide rings of XXI or XXIII can be opened with a halogenating agent, such as hydrogen fluoride in pyridine, to form the halohydrin, and then reacted with a second halogenating agent, such as diethylaminosulfurtrifluoride (DAST), to produce the tetrahalo compounds of formula:

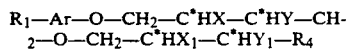

$$R_1-Ar-O-CH_2-C^*HX-C^*HY-CH_2-O-CH_2-C^*HX_1-C^*HY_1-R_4$$

where $X_1$ and $Y_1$ are halides which can be the same or different, and where chlorine and fluorine are preferred. $R_4$ is an alkyl or alkenyl.

Some of the compounds produced by derivitization method D include compounds XXII and XXIV of Table 2. Complete descriptions of each compound are provided in the Examples.

Many of the compounds of the subject invention do not possess an enantiotropic or monotropic ferroelectric (smectic C*) liquid crystal phase. However, when compounds of the subject invention such as those in Table 2 are mixed with a known FLC host material, such as W82, mixtures are produced which possess ferroelectric smectic C* phases with improved polarization densities relative to that of the host material alone. W82 has a very low polarization density of the order of $-1$ $nC/cm^2$. The subject compositions can improve the polarization densities of FLC mixtures without significantly increasing the orientational viscosity of the mixture. The subject compositions can be used as compensating agents for the N* or C* helical pitch of an FLC composition.

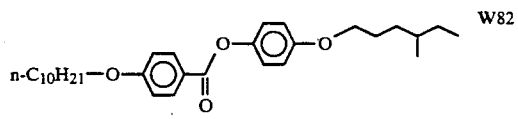

Table 2 summarizes the mesomorphic properties, extrapolated polarization density and phase transition temperatures of 10% (w/w) mixtures of subject compositions with W82. In Table 2, the phases are noted as X=crystal, I=isotropic liquid, A=smectic A, C*=smectic C, S=undefined smectic phase, and phase transition temperatures are given in °C. $P_{ext}$ is the polarization density as extrapolated from a 10% by weight mixture of the subject composition in W82. $P_{ext}$ is given in $nC/cm^2$ and the

TABLE 2

Conversion of difluoroalcohol IXa or IXb into various derivatives.

$$R_1-ArO\diagdown\overset{Y}{\underset{X}{\diagup}}\diagdown OH \xrightarrow{Method} C_nH_{2n+1}-\diagdown\overset{N}{\underset{N}{\diagup}}\diagdown-\diagdown-O\diagdown\overset{Y}{\underset{X}{\diagup}}\diagdown OR_2$$

| $R_z$ | Cpd # | n | Method | $P_{ext}$ | θ | Mesomorphic Properties | Phase Diagram of Mixture (10%) |
|---|---|---|---|---|---|---|---|
| ![](acetyl H) | X | 6 | A | 230 | | S 54°↗ ↘67° X↖ ↙I 36°↖ ↙40° A | |
| ![](acetyl CH3) | XI | 6 | B | 350 | 22° | | X—80°→I |
| ![](acetyl CH3) | XII | 7 | B | 410 | 27° | | X←26°—C←63°—A←68.5°—I |
| | XIII | 6 | B | 396 | 23° | | X—83°→I  X←74°—I |

TABLE 2-continued

Conversion of difluoroalcohol IXa or IXb into various derivatives.

$$R_1-ArO-\overset{Y}{\underset{X}{CH}}-OH \xrightarrow{\text{Method}} C_nH_{2n+1}-\text{[pyrimidine]}-\text{[phenyl]}-O-\overset{Y}{\underset{X}{CH}}-OR_2$$

| $R_z$ | Cpd # | n | Method | $P_{ext}$ | θ | Mesomorphic Properties | Phase Diagram of Mixture (10%) |
|---|---|---|---|---|---|---|---|
| (pentanoyl) | XIV | 6 | B | 416 | 22° | X —80°→ I<br>X ←74°— I | |
| (heptanoyl) | XV | 7 | B | 374 | 28° | X —74°→ I<br>X ←72°— I | X ←27°— C ←60°— A ←68°— I |
| (hexenoyl) | XVI | 6 | B | 437 | 28° | | |
| (methyl ether) | XVII | 7 | C | 190 | 27° | X —70°→ I | |
| (alkyl) | XVIII | 7 | C | 220 | 28° | X —53°→ I | X ←23°— C ←57.2°— A ←67.2°— I |
| (alkenyl) | XIX | 6 | C | | | | |
| (branched alkyl) | XX | 6 | C | 22 | 21° | liq. at 20° | X ←23°— C ←46°— A ←60°— I |
| (R,R) epoxide | XXI | 6 | C | 125 | | X —46°→ I<br>X ←24°— I | |
| difluoro (F,F) | XXII | 6 | D | 240 | | X ⇌ 73°/70° I | |
| (S,S) epoxide | XXIII | 6 | C | 204 | | X ⇌ 76°/70° I | |
| monofluoro F | XXIV | 6 | D | 101 | | X —68°→ I<br>X ←58°— I | | polarization magnitude was measured by integration of the dynamic current response on reversing the applied electric field, as described in Martinot-Lagarde (1976) J. Phys. 37, C-3, p.129 and Martinot-Lagarde (1977) J. Phys. Lett. 38, L-17.

Compositions of the subject invention can also be admixed with host materials in any desired weight percentage. Generally, as the weight percentage of subject compositions in the host material is increased linearly. Depending on the intended application and desired polarization of the FLC mixture, a person of skill in the art can determine the appropriate concentration of subject compositions to incorporate in a host material to obtain the desired polarization. Because the polarization densities of the subject applications are high, low concentrations are typically used as dopants to obtain the desired polarization in the mixture. Generally, the concentrations of the dopants used in the host are less than about 20% (w/w). Such low concentrations avoid orientational viscosity that may be associated with the use of higher concentrations of such dopants.

Compositions of the subject invention can be mixed with any suitable host material. Suitable host materials vary with the intended application, but generally, solubility or miscibility with the dopant, broad C* phase temperature range (e.g., −20° C. to 60 ° C.) and low orientational viscosity are considered desirable.

An important aspect of the present invention is the finding that some of the compounds having proximal segments of formulas IXa and IXb (Q=R₂), can have improved polarization properties as FLC dopants relative to those of analogous compounds having only one oxygen in the chiral tail:

| Analogous Compound | Tilt | $P_{ext}$ |
| --- | --- | --- |
| 4'-(2S,3S-difluorohexyloxy)phenyl-5-hexylpyrimidine | 25° | 300 nC/cm$^2$ |
| 4'-(2S,3S-difluorohexyloxy)phenyl-5-heptylpyrimidine | 25° | 280 nC/cm$^2$ |

As can be seen from Table 2, the esters, XI, XIII, XIV, and XVI, show improved extrapolated polarization relative to 4'-(2S,3S-difluorohexyloxy-phenyl-5-hexylpyrimidine. The esters, XII and XV, also show improved extrapolated polarization relative to 4'-(2S,3S-difluorohexyloxy)phenyl-5-heptylpyrimidine.

For comparison with the subject compositions of Table 2, the $P_{ext}$ for these analogous compounds is the extrapolated polarization from a 10% by weight mixture of the compounds in W82.

The improved polarization of the subject compositions is believed to be due to the relative alignment of the dipoles of the halide(s) and oxygens of the chiral tail. It should be noted that it is dipole orientation of the subject conformations in the oriented smectic C phase that affects polarization density. Only the components of the dipoles normal to the tilt plane affect polarization. The structure of the proximal and distal segments of the achiral tail and any steric and/or electronic interaction between the groups will affect dipole orientation and the magnitude and sign of the polarization density. The relationship between dipole alignment and ferroelectric polarization density has been discussed for related molecules in Walba et al. (1986) J. Amer. Chem. Soc. 108:5210–5221 and Walba et al. (1986) J. Amer. Chem. Soc. 108:7424–7425, both of which are incorporated herein by reference.

As exemplified herein, the incorporation of the proximal chiral segment of the subject invention,—O—CH$_2$—C*HX—C*HY—CH$_2$—O—, and any of a variety of distal segments described herein, into an FLC compound can produce an FLC dopant that demonstrates improved polarization properties.

EXAMPLES

Example

Synthesis of 2-[4'-(2R,3R-dihalo-4-hydroxy)butyloxy]phenyl-5-R$_1$-pyrimidines

This example illustrates the synthesis of chiral 2-[4'-(2,3-dihalo-4-hydroxy)butyloxy]phenyl-5-R$_1$-pyrimidines. The procedure is illustrated by the synthesis of the difluoride, 2-[4'-(2R,3R-difluoro-4-hydroxy)-butyloxy]phenyl-5-hexylpyridine (IXa, where R$_1$=hexyl, Q=H, Ar=2-phenylpyrimidine, and X and Y=F).

Initially, L-diethyl tartrate (Ia) (150 g or 728 mmol), dimethoxypropane (179 ml or 1.45 mol), and toluenesulfonic acid (TsOH) (2.78 g or 14.6 mmol) were added to a 500 ml flame-dried flask containing a magnetic stir bar. The reaction was allowed to stir 12 hours, and then an additional 90 ml (0.73 mol) dimethoxypropane was added. The reaction was allowed to stir an additional 24 hours, at which time approximately 160 ml of the solution was removed by fractional distillation, after which an additional 90 ml (0.73 mol) dimethoxypropane was added. Approximately one hour later, the reaction mixture was poured into a 10% aqueous NaHCO3 solution and extracted with a 1:1 (v/v) hexane:ethyl acetate solvent mixture. The combined organic layers were then extracted with saturated NaCl, dried over a mixture of anhydrous Na$_2$SO$_4$ and K$_2$CO$_3$, and the solvent was removed in vacuo to produce a dark oil. The oil was then fractionally distilled at 110°–120° C., giving a yield of 128 g of a 1:1 (by gas chromatograph) mixture of the desired acetonide (II) and an unidentified side product.

To a three liter oven-dried 3-neck flask equipped with a mechanical stirring rod, an addition funnel, and a condenser, was added 29.6 g (0.78 mol) lithium aluminum hydride (LAH) and 1.5 l dry ether. To the addition funnel was then added to the acetonide (II) mixture and approximately 300 ml ether. The LAH suspension was stirred at a rapid rate and cooled in an ice bath to 0° C. The acetonide solution was then allowed to slowly drip into the suspension over the course of approximately 40 minutes, after which the ice bath was removed and the reaction was allowed to stir a further 90 minutes. The ice bath was then replaced and the reaction mixture was treated by dropwise addition of 29.2 ml of water, 29.6 ml of a 1.5 g/l aqueous NaOH solution, and 89 ml water. The suspension was allowed to stir overnight. To the suspension was added 20 g anhydrous MgSO$_4$, and after a further 15 minutes stirring, the reaction mixture was filtered through a 1 inch pad of celite, which was washed with ether, and the solvent was removed in vacuo. The resulting yellow oil was distilled at 112° C. at 3 mm Hg to give 38.6 g (33% yield over two steps) of the product, 2S,3S-isopropylidenethreitol (III), as a clear oil.

Next, 2S,3S-isopropylidenethreitol (III) (20 g or 123 mmol), benzyl chloride (14.19 ml or 123 mmole), dichloromethane (78 ml), NaOH solution (90.6 ml of 4M), and tetrabutylammonium bromide (1.99 g or 6.2 mmol) were added to a 500 ml flask containing a magnetic stir bar. A reflux condensor was attached to the top of the flask, and the biphasic reaction was allowed to reflux with stirring for about 30 hours. The reaction mixture was then poured into a separatory funnel and the layers were separated. The aqueous layer was extracted twice more with dichloromethane. The combined organic layers were dried over a mixture of anhydrous Na$_2$SO$_4$ and K$_2$CO$_3$, and the solvent was removed in vacuo. The oil was then fractionally distilled, with the product, 4-benzyloxy-2S,3S-isopropylidenethreitol (IV), coming over at 138° C. (3mm Hg) to give a yield of 20.9 g (67% yield).

Next, 2S,3S-acetonide-4-benzyloxythreitol (IV) (6.543 g or 25.9 mmol) and toluenesulfonyl chloride (9.888 g or 51.9 mmol) were added to a 250 ml flame-dried flask containing a magnetic stir bar. The flask was cooled in an ice bath, and 78 ml of ice-cold anhydrous pyridine was added. The reaction mixture was stirred in the ice bath for one hour, then allowed to sit in a −20° C. cooler overnight. The reaction mixture was poured into water and extracted three times with diethyl ether. The combined organic layers were then extracted with a saturated NaCl solution, dried over anhydrous sodium sulfate, and the solvents removed in vacuo to give 10.25 g (98% yield) of 4-benzyloxy-2S,3S-isopropylidene-1-(4-toluenesulfonate)threitol (V) as a viscous oil.

To produce 2-{([4'-(4-benzyloxy-2S,3S-O-isopropylidenedioxy)-butyloxy]}phenyl-5-hexylpyrimidine; 4-benzyloxy-2S,3S-isopropylidene-1-(4-toluenesulfonate)threitol (V) (2.00 g or 5.0 mmol), 4-hexylpyrimidylphenol (R$_1$—ArOH, where R$_1$=hexyl)

(1.525 g or 6.0 mmol) and dimethylformamide (15 ml) were added to a 25 ml flame-dried flask containing a magnetic stir bar. The mixture was stirred while 274 mg (5.7 mmol) of a 1:1 (w/w) NaH/mineral oil mixture was slowly added. The reaction was allowed to stir overnight at which time it was heated to 73° C. to force the reaction to completion. The reaction mixture was then poured into 25 ml of water, and extracted with a 1:1 (v/v) hexane:ethyl acetate solvent mixture. The combined organic layers were then extracted with saturated NaCl, dried over a mixture of anhydrous sodium sulfate and potassium carbonate, and the solvent was removed in vacuo. The product was purified by flash chromoatography using a 35 mm silica gel column and a 4:1 hexane:ethyl acetate solvent to afford 2.36 g (97% yield) of the desired product, 2-{[4'-(4-benzyloxy-2S,3S-O-isopropylidenedioxy)butyloxy]}phenyl-5-hexylpyrimidine (VI, where $R_1$=hexyl), as a waxy solid.

To obtain 2-[4'-(4-benzyloxy -2S,3S -dihydroxy)-butyloxy]phenyl-5-hexylpyrimidine; 2-{[4'-(4-benzyloxy-2S,3S-0-isopropylidenedioxy)butyloxy]}phenyl-5-hexylpyrimidine (2.08 g or 4.2 mmol), tetrahydrofuran (16 ml), water (12 ml), and concentrated HCl (3.5 ml) were added to a 50 ml flask containing a magnetic stir bar. The reaction was allowed to stir (approximately 8 hours) until no further starting material remained as evidenced by TLC. The reaction mixture was then poured into water and extracted with ether. The combined organic layers were then extracted with saturated NaCl, dried over a mixture of anhydrous $Na_2SO_4$ and $K_2CO_3$, and the solvent was removed in vacuo. The reaction was purified by flash chromatography on silica gel using 1:1 (v/v) hexane:ethyl acetate as an eluent, affording 191 g (100% yield) of the 2-[4'-(4-benzyloxy-2S,3S-dihydroxy)butyloxy]phenyl-5-hexylpyrimidine (VII, where $R_1$=hexyl), as a waxy solid.

To make 2-[4'-4-benzyloxy-2S,3S-difluoro)butyloxy]-phenyl-hexylpyrimidine; 1.52 g (3.37 mmol) of 2-[4'-(4-benzyloxy-S,3S-dihydroxybutyloxy)]phenyl-5-hexylpyrimidine and 40 ml of dichloromethane were added to a flame-dried 50 ml flask containing a magnetic stir bar. The solution was cooled to −78° C. with stirring, and 2.7 ml (20 mmol) of DAST were slowly added. The reaction was allowed to warm to −30° C. over the course of an hour, at which time 2.3 ml (28 mmol) of anhydrous pyridine were added. The reaction was slowly warmed to room temperature and allowed to stir overnight. The reaction mixture was then slowly added to a 10% aqueous $NaHCO_3$ solution, from which it was extracted with methlylene chloride. The combined organic layers were then dried over a mixture of anhydrous $Na_2SO_4$ and $K_2CO_3$, and the solvent was removed in vacuo. The product was then purified by flash chromoatography on a silica column using 4:1 (v/v) hexane:ethyl acetate as the eluent, affording 838 mg (55% yield) of 2-[4'-(4-benzyloxy-2S,3S-difluoro)-butyloxy]phenyl-5-hexylpyrimidine (VIII, where $R_1$=hexyl and X and Y=F), as a viscous oil.

To make 2-[4'-(2R,3R-difluoro-4-hydroxy)butyloxy]-phenyl-5-hexylpyrimidine; 838 mg (1.84 mmol) of 2-[4'-4-benzyloxy-2S,3S-difluorobutyloxy)]phenyl-5-hexylpyrimidine and 10 ml of methylene chloride were added to a 50 ml flame-dried flask containing a magnetic stir bar. The stirred solution was cooled to 0° C. and 2.03 ml of a 1 M $BBr_3$ solution was slowly added over 5 minutes while stirring. The reaction was stirred a further 15 minutes, at which time the reaction mixture was slowly added to a 10% (w/v) $NaHCO_3$ solution, from which it was extracted with methylene chloride. The combined organic layers were then dried over a mixture of anhydrous $Na_2SO_4$ and $K_2CO_3$, and the solvent was removed in vacuo. The product was then purified by flash chromatography on a silica column using 3:2 (v/v) hexane:ethyl acetate as the eluent, affording 540 mg (80% yield) of 2-[4'-(2R,3R-difluoro-hydroxy)butyloxy]phenyl-5-hexylpyrimidine (IXa, where $R_1$=hexyl, X and Y=F and Q=H).

Example 1a

Synthesis of Compounds containing the chiral 2R,3R-dihalo-4-hydroxybutyloxy segment coupled to other $R_1$-substituted Cores In the synthesis of compound VI from compound V in Scheme 1, any 4-$R_1$-4'-hydroxy substituted FLC core ($R_1$—ArOH) can be used. For example, the synthesis of 4'-phenol-5-alkylpyridine is described in Ohno et al., U.S. Pat. No. 4,795,587 (1989) (see compound V therein). 4'-phenol-5-alkylpyridine can then be used in the method of Example 1 to synthesize many different chiral 4- alkylphenyl-4'-(2R,3R-dihalo-4-hydroxybutyloxy)pyrimidine compounds, having a variety of achiral tails.

Other $R_1$-ArOH compounds such as 4-$R_1$-4'-hydroxybiphenyl, 4-$R_1$-phenyl-4'-hydroxybenzoate, 4-hydroxyphenyl-4'$R_1$-benzoate, and other $R_1$-substituted core units using cores described hereinabove are commercially available or can be synthesized by methods known in the art from readily available starting materials.

Other $R_1$-ArOH compounds can be used in the synthesis of all IXa and IXb (Q=H) enantiomers and regioisomers of the subject invention.

Example 2

Synthesis of 2-(4'-2S,3S-dihalo-4-hydroxybutyloxy) phenyl-5-R -pyrimidines

This example illustrates the synthesis of chiral 2-[4'-(2S,3S-dihalo-4-hydroxy)butyloxy]phenyl-5-alkylpyrimidines(IXb, where Q=H, Ar=2-phenylpyrimidine, and X and Y=halides). This method can be used to obtain the enantiomers of compounds produced by the methods of any of the Examples described herein. The method for obtaining 2-(4'-2S,3S-dihalo-4-hydroxybutyloxy)phenyl-5-$R_1$-pyrimidines is substantially the same as the method described in Example 1 with the exception that compound Ia, L-diethyl tartrate, is replaced with its enantiomer, Ib, D-diethyl tartrate D-diethyl tartrate, like L-diethyl tartrate, is commercially available.

The enantiomer of the compound produced by Example 1, when the D-diethyl tartrate is used in place of L-diethyl tartrate, is 2-[4'-(2S,3S-difluoro-4-hydroxy)-butyloxy]phenyl-5-hexylpyrimidine.

Example 3

Synthesis of 4'-(2R,3R-difluoro-4-formyl-butyloxy)phenyl-4-n-hexylpyrimidine (X)

To make compound X, 30 mg (82 μmol) of 2-[4'-(2R,3R-difluoro-4-hydroxybuyloxy)]phenyl-5-hexylpyrimidine (IXa, where R=hexyl, Q=H and X and Y=F) and 10 ml of methyl formate were added to a 10 ml flame-dried flask containing a magnetic stir bar. Approximately 10 μl titatnium isopropoxide was then added to the solution as a transesterification catalyst, and the reaction was stirred 12 hours. At this time a further 10 μl catalyst was added, and the milky white reaction was stirred for five minutes, at which time it was poured into water and extracted with ether. The combined organic phases were washed with a saturated NaCl solution, dried over a mixture of anhydrous $Na_2SO_4$ and $K_2CSO_3$, and the solvent was removed in vacuo. The product was purified by flash chromatography on a silica column using 3:2 (v/v) hexanes:ethyl acetate as the eluent, affording 28.0 mg (87% yield) of 4'-(2R,3R-difluoro-4-formyl-butyloxy)phenyl-4-n-hexylpyrimidine (X).

Example 4

Syntheses of
4'-(2R,3R-difluoro-4-alkylester-butyloxy)phenyl-4-alkylpyrimidines (XI–XV) and
4'-(2R,3R-difluoro-4-alkenylester-butyloxy)phenyl-4-alkylpyrimidines (XVI) Example 4a Synthesis of
4'-(2R,3R-difluoro-4-acetyl-butyloxy)phenyl-4-n-hexylpyrimidine (XI)

To make compound XI, 55 mg (.151 mmol) of 2-[4'-(2R,3R-difluoro-4-hydroxy)butyloxy]phenyl-5-hexylpyrimidine (IXa, where $R_1$=hexyl, Q=H and X and Y=F), 33 μl (0.45 mmol) of acetic anhydride, 110 μl (1.4 mmol) of pyridine, 1.5 ml of THF, and about 2 mg of DMAP were added to a 10 ml flame-dried flask containing a magnetic stir bar. The reaction was allowed to stir overnight. It was then poured into water and extracted with ether. The combined organic phases were washed once each with a dilute NaOH and a saturated NaCl solution, dried over a mixture of anhydrous $Na_2SO_4$ and $K_2CSO_3$, and the solvent was removed in vacuo. The product was purified by flash chromatography on a silica column using 4:1 (v/v) hexanes:ethyl acetate as the eluent, affording 46.2 mg (75%) yield of the product, 4'-(2R,3R-difluoro-4-acetyl-butyloxy)phenyl-4-n-hexylpyrimidine (XI).

Example 4b

Synthesis of
4'-(2R,3R-difluoro-4-acetylbutyloxy)phenyl-4-n-heptylpyrimidine (XII)

To make compound XII, the same procedure for making compound XI was followed with the exception that 2-[4'-(2R,3R-difluoro-4-hydroxy)butyloxy]phenyl-5-heptylpyrimidine (IXa, where $R_1$=heptyl, Q=H and X and Y=F) was used in place of 2-[4'-(2R,3R-difluoro-4-hydroxy)butyloxy]phenyl-5-hexylpyrimidine.

Example 4

Synthesis of
4'-[(2R,3R-difluoro-4-propanoate)butyloxy]phenyl-4-hexylpyrimidine (XIII)

To make compound XIII, the procedure for making compound XI was followed with the exception that propanoyl chloride was used in place of acetic anhydride.

Example 4d

Synthesis of
4'-[(2R,3R-difluoro-4-butanoate)butyloxy]phenyl-4-hexylpyrimidine (XIV)

To make compound XIV, the procedure for making compound XI was followed with the exception that butanoyl chloride was used in place of acetic anhydride.

Example 4e

Synthesis of
4'-[(2R,3R-difluoro-4-pentanoate)butyloxy]phenyl-4-heptylpyrimidine (XV)

To make compound XV, the procedure for making compound XII was followed with the exception that pentanoyl chloride was used in place of acetic anhydride.

Example 4f

Synthesis of
4'-{[2R,3R-difluoro-4-(4-pentenoate)]-butyloxy}phenyl-4-hexylpyrimidine (XVI)

To make compound XVI, the procedure for making compound XI was followed with the exception that 4-pentenoyl chloride was used in place of acetic anhydride.

Example 5

Syntheses of
4'-[(2R,3R-dihalo-4-alkoxy)butyloxy]phenyl-4-alkylpyrimidines and
4'-[2R,3R-dihalo-4-(epoxyalkoxy)butyloxy]phenyl-4-alkylpyrimidines (XVII, XVIII, XIX, XX, XXI, XXIII)

Example 5a

Synthesis of
4'-[(2R,3R-difluoro-4-methoxy)butyloxy]phenyl-4-heptylpyrimidine (XVII)

To make compound XVII, 18.6 mg (49 μmol) of 2-[4'-(2R,3R-difluoro-4-hydroxy)butyloxy]phenyl-5-heptylpyrimidine and 4 ml of THF were added to a 10 ml flame-dried flask containing a 2 magnetic stir bar. To this solution was added 5 mg (98 μmol) of a 1:1 (w/w) NaH/mineral oil mixture, 12 μl (200 μmol) of methyl iodide, and 1 ml DMF. The reaction was allowed to stir overnight. The reaction was then poured into water and extracted with 1:1 (v/v) hexane:ethyl acetate. The combined organic layers were then extracted with saturated NaCl, dried over a mixture of anhydrous $Na_2SO_4$ and $K_2CO_3$, and the solvent was removed in vacuo The reaction mixture was purified by flash chromatography on a silica column using 4:1 (v/v) hexane:ethyl acetate as an eluent, affording 16.3 mg (84%) of 4'-[(2R,3R-difluoro-4-methoxy)butyloxy]phenyl-4-heptylpyrimidine (XVII).

Example 5b

Synthesis of
4'-[(2R,3R-difluoro-4-butyloxy)butyloxy]phenyl-4-heptylpyrimidine (XVIII)

To make compound XVIII, the method for making compound XVII was followed with the exception that 1-butyl iodide was used in place of methyl iodide.

Example 5c

Synthesis of 4'-[2R,3R-difluoro-4-(4-pentenoxy)butyloxy]phenyl-4-hexylpyrimidine (XIX)

To make compound XIX, the method for making compound XVII was followed with the exceptions that: (1) 2-[4'-(2R,3R-difluoro-4-hydroxy)butyloxy]phenyl-5-hexylpyrimidine was used instead of 2-[4'-(2R,3R-difluoro-4-hydroxy)butyloxy]phenyl-5-heptylpyrimidine, and (2) 4-pentenyl iodide was used instead of methyl iodide.

Example 5d

Synthesis of 4'-[2R,3R-difluoro-4-(1-methylheptyloxy)butyloxy]phenyl-4-hexylpyrimidine (XX)

To synthesize compound XX, the method for making compound with the exceptions that: (1) XVII was followed 2-[4'-(2R,3R-difluoro-4-hydroxy)butyloxy]phenyl-5-hexylpyrimidine was used instead of 2-[4'-(2R,3R-difluoro-4-hydroxy)butyloxy]phenyl-5-heptylpyrimidine, and (2) 1-methylheptyl iodide was used instead of methyl iodide.

Example 5e

Synthesis 4'-{[2R,3R-difluoro-4-(2R,3R-epoxy)hexyloxy]butyloxy}phenyl-4-hexylpyrimidine (XXI)

To synthesize compound XXI, the method for making compound XVII was followed with the exceptions that: (1) 2-[4'-(2R,3R-difluoro-4-hydroxy)butyloxy]phenyl-5-hexylpyrimidine was used instead of 2-[4'-(2R,3R-difluoro-4-hydroxy)butyloxy]phenyl-5-heptylpyrimidine, and (2) 2R,3R-epoxyhexyl tosylate was used in place of methyl iodide.

Example 5f

Synthesis of 4'-{[2R,3R-difluoro-4-(2S,3S-epoxy)hexyloxy]butyloxy}phenyl-4-hexylpyrimidine (XXIII)

To synthesize compound XXIII, the method for making compound XVII was followed with the exceptions that: (1) 2-[4'-(2R,3R-difluoro-4-hydroxy)butyloxy]phenyl-5-hexylpyrimidine was used instead of 2-[4'-(2R,3R-difluoro-4-hydroxy)butyloxy]phenyl-5-heptylpyrimidine, and (2) 2S,3S-epoxyhexyl tosylate was used in place of methyl iodide.

Example 6

Synthesis of chiral 4'-[2,3-dihalo-4-(2,3-dihaloalkoxy)butyloxy]phenyl-4-alkylpyrimidines Example 6a Synthesis of 4'-[2R,3R-difluoro-4-(2S,3S-difluorohexyloxy)butyloxy]phenyl-4-hexylpyrimidine (XXIV)

To synthesize compound XXIV, 57.1 mg (0.123 mmol) of compound XXIII and 1.0 ml of dichloromethane were added to a 20 ml polyethylene bottle containing a magnetic stir bar. The solution was cooled to 0° C. 35 μl (1.2 mmol) of a commercial mixture of hydrogen fluoride in pyridine was then added, and the reaction was allowed to stir for approximately three hours, at which time the reaction was judged complete by TLC analysis. The reaction mixture was then poured into dilute $Na_2CO_3$ solution, from which it was extracted with dichloromethane. The combined organic layers were then dried over a mixture of anhydrous $Na_2SO_4$ and $K_2CO_3$, and the solvent was removed in vacuo to give the fluorohydrin.

The fluorohydrin was then dissolved in 1.2 ml of dry dichloromethane and transferred into a flame-dried 10 ml flask containing a magnetic stir bar. The solution was cooled to −78° C. and 49 μl (0.37 mmol) diethylaminosulfurtrifluoride (DAST) was added. The reaction was allowed to warm to −30° C. over the course of an hour, at which time 40 μl (0.49 mmol) anhydrous pyridine was added. The reaction was allowed to warm to room temperature and was stirred overnight. The reaction mixture was then slowly poured into a dilute $NaHCO_3$ solution, from which it was extracted with dichloromethane. The combined organic layers were dried over a mixture of anhydrous $Na_2SO_4$ and $K_2CO_3$, and the solvent was removed in vacuo. The reaction mixture was purified by flash chromatography on a silica gel column successively using 9:1 (v/v) and 4:1 (v/v) hexane:ethyl acetate as eluents, affording 19.7 mg (33%) of the tetrafluoro compound, XXIV. $^{19}$NMR of this compound shows three multiplets, two of equal size at −199.5 and −203.8, the other twice that size at −205.5; $^1$H NMR shows a five multiplet group centered at 5.0 δ and a four multiplet group centered at 4.6 δ.

Example 6b

Synthesis of 4'-[2R,3R-difluoro-4-(2R,3R-difluorohexyloxy)butyloxy]phenyl-4-hexylpyrimidine (XXII)

To synthesize compound XXII, the method for making compound XXIV was followed with the exception that compound XXI was used in place of compound XXIII.

This invention has been described and illustrated by reference to several preferred embodiments, but it is not intended to limit the invention by doing so. It is intended that the invention encompass all enantiomers and regioisomers of the general formula:

where the proximal segment is a 2R,3R-dihalo or a 2S,3S-dihalo. It is also intended that the invention include mixtures of two or more compositions of the subject invention, and FLC formulations in which these compounds are admixed with each other or with other compounds including LC and FLC materials.

We claim:

1. A chiral nonracemic compound of the formula:

wherein

* denotes a chiral carbon,

X and Y are halogens selected from the group of chlorine and fluorine, the —O—CH$_2$—C*HX—C—HY—CH$_2$—O— segment comprises the chiral proximal segment of the chiral tails, said proximal segment being selected from the enantiomers 2R,3R-dihalo and 2S,3S-dihalo, R$_1$ is an achiral alkyl, alkyl sulfide, alkyl ether, alkenyl, alkenyl sulfide, alkenyl ether, alkoxy, alkoxy sulfide, or alkoxy ether group of two to sixteen carbons, Ar is an achiral FLC core selected from the group consisting of phenylbenzoates, phenylpyrimidines, biphenyls, phenylpyridines, biphenylbenzoates, diphenylpyrimidines, diphenylpyridines, terphenyls, phenyldiazenes, diphenyldiazenes, and diphenylthiadiazoles, with the chiral proximal segment and $R_1$ para-substituted with respect to each other on outer rings of said core, and $R_2$ is a distal segment of the chiral tail comprising one to ten carbon atoms and is selected from the group consisting of aldehyde, alkyl acyl, alkyl, alkenyl, alkenyl acyl, alkyl halide, alkenyl halide, alkyl epoxide, and alkenyl epoxide.

2. The compound of claim 1, wherein $R_1$ comprises five to sixteen carbons.

3. The compound of claim 4, wherein $R_1$ comprises eight carbons.

4. The compound of claim 1, wherein $R_1$ is selected from the group of straight-chain or branched.

5. The compound of claim 1, wherein $R_2$ comprises three carbons.

6. The compound of claim 1, wherein $R_2$ is selected from the group of straight-chain and branched.

7. The compound of claim 1, wherein $R_2$ comprises a chiral carbon.

8. The compound of claim 1, wherein $R_2$ is an alkyl halide consisting of two halogens.

9. The compound of claim 1, wherein said alkyl halides comprise fluorine or chlorine.

10. The compound of claim 1, wherein said composition is selected from the group consisting of 4'-[(2R,3R-difluoro-4-formyl)-butyloxy]phenyl-4-hexylpyrimidine (X); 4'-[(2R,3R-difluoro-4-acetyl)butyloxy]phenyl-4-hexylpyrimidine (XI); 4'-[(2R,3R-difluoro-4-acetyl)-butyloxy]phenyl-4-heptylpyrimidine (XII); 4'-[(2R,3R-difluoro-4-propanoate)butyloxy]phenyl-4-hexylpyrimidine (XIII); 4'-[(2R,3R-difluoro-4-butanoate)-butyloxy]phenyl-4-hexylpyrimidine (XIV); 4'-[(2R,3R-difluoro-4-pentanoate)butyloxy]phenyl-4-heptylpyrimidine (XV); 4'-[2R,3R-difluoro-4-(4-pentenoate)-butyloxy]phenyl-4-hexylpyrimidine (XVI); 4'-[2R,3R-difluoro-4-methoxy)butyloxy]-phenyl-4-heptylpyrimidine (XVII); 4'-[(2R,3R-difluoro-4-butyloxy) butanoxy]phenyl-4-heptylpyrimidine (XVIII); 4'-(2R,3R-difluoro-4-(4-pentenoxy)-butyloxy)phenyl-4-hexylpyrimidine (XIX); 4'-(2R,3R-difluoro-4-(1-methylheptyloxy)buty oxy)- phenyl-4-hexylpyrimidine (XX); 4'-{[2R,3R-difluoro-4-(2R,3R-epoxy)hexyloxy]butyloxy} phenyl-4-hexylpy (XXI);4'-{[2R,3R-difluoro-4-(2S,3S-epoxy)hexyloxy]butyloxy}phenyl-4-hexylpyrimidine (XXIII); 4'-[2R,3R-difluoro-4-(2S,3S-difluorohexyloxy)butyloxy]phenyl-4-hexylpyrimidine (XXIV); and 4'-[2R,3R-difluoro-4-(2R,3R-difluorohexyloxy)butyloxy]-phenyl-4-hexylprimidine (XXII).

11. An FLC composition comprising the compound of claim 1.

* * * * *